United States Patent [19]
Hoath et al.

[11] Patent Number: 6,113,932
[45] Date of Patent: Sep. 5, 2000

[54] NONTOXIC VERNIX COMPOSITIONS AND METHOD OF PRODUCING

[75] Inventors: Steven B. Hoath; William L. Pickens; Martha O. Visscher, all of Cincinnati, Ohio

[73] Assignee: Children's Hospital Medical Center, Cincinnati, Ohio

[21] Appl. No.: 09/257,008

[22] Filed: Feb. 25, 1999

Related U.S. Application Data

[63] Continuation-in-part of application No. 09/033,209, Mar. 2, 1998.

[51] Int. Cl.⁷ .................................................. A01N 25/35
[52] U.S. Cl. ........................ 424/402; 424/59; 424/401; 424/443; 424/444; 424/445
[58] Field of Search ............................. 424/59, 401, 402, 424/443, 444, 445

[56] References Cited

U.S. PATENT DOCUMENTS

| | | | |
|---|---|---|---|
| 3,655,416 | 4/1972 | Vinson, et al. | 106/155 |
| 3,660,566 | 5/1972 | Vinson, et al. | 424/95 |
| 4,366,169 | 12/1982 | White | 424/285 |
| 4,428,965 | 1/1984 | Elsohly et al. | 424/311 |
| 4,451,453 | 5/1984 | Lay et al. | 424/81 |
| 4,569,784 | 2/1986 | Moore | 252/315.1 |
| 4,997,649 | 3/1991 | Papaconstantin et al. | 424/195.1 |
| 5,049,580 | 9/1991 | Crouthamel | 514/424 |
| 5,215,759 | 6/1993 | Mausner | 424/489 |
| 5,540,964 | 7/1996 | Mallen | 428/36.1 |
| 5,631,012 | 5/1997 | Shanni | 424/401 |
| 5,871,763 | 2/1999 | Luu et al. | 424/402 |

FOREIGN PATENT DOCUMENTS 2 614 787  11/1988  France .
1718947A1  1/1987  U.S.S.R. .

OTHER PUBLICATIONS

V.M. Joglekar, Barrier properties of vernix caseosa, Archives of Disease in Childhood, vol. 55 (No. 10) 817–819, 1980.

Theodoros Agorastos, M.C., et al., Features of Vernix Caeseosa Cells, American Journal of Perinatology, vol. 5, No. 3, Jul. 1988.

N. Nicolaides et al., Further Studies of the Saturated Methyl Branched Fatty Acids of Vernix Caseosa Lipid, LIPIDS, vol. 11, No. 11.

N. Nicolaides, The Structures of the Branched Fatty Acids in the Wax Esters of Vernix Caseosa, LIPIDS vol. 6 No. 12.

J.F. Stadler; D. Saint–Leger, A.M. francois, 1. Schreiber, P. lopez, B. dreno, Abstract, Topographical Variations of the Composition of Vernix Caseosa, Annual Meeting of the Dermatological Research Society, Nantes, France Oct. 9, 10, 11, 1986.

Mary Ellen Stewart, Ph.D.; Mara A. Quinn, B.S., Variability in the Fatty Acid Composition of Wax Esters from Vernix Caseosa and Its Possible Relation to Sebaceous Gland Activity, The Journal of Investigative Dermatology, 78:291–295, 1982 vol. 78 No. 4.

*Primary Examiner*—S. Mark Clardy
*Assistant Examiner*—Kathryne E. Shelborne
*Attorney, Agent, or Firm*—Wood, Herron & Evans L.L.P.

[57] ABSTRACT

A composition consisting essentially of vernix for a skin curative and skin protectant effect and a method of producing. A natural or synthetic vernix is dispersed in a film-forming amount in a biocompatable liquid such as dimethylsulfoxide, amniotic fluid and/or pulmonary surfactant to form a film. The film may be applied to a growing layer of epithelial cells either directly or supported on a substrate such as a wound dressing, a diaper, or a feminine hygiene product.

36 Claims, 5 Drawing Sheets

NONTOXIC VERNIX COMPOSITIONS AND METHOD OF PRODUCING

RELATED APPLICATIONS

This application is a Continuation-In-Part application of U.S. application Ser. No. 09/033,209 filed Mar. 2, 1998, now pending.

The U.S. Government has a paid-up license in this invention and the right in limited circumstances to require the patent owner to license others on reasonable terms as provided for by the terms of Grant No. 5 R01 NR 03699-05 awarded by the National Institutes of Health.

FIELD OF THE INVENTION

The invention relates generally to a therapeutic or prophylactic, natural or synthetic vernix film for enhanced growth and maturation of skin and other tissue.

BACKGROUND OF THE INVENTION

Skin is one of the largest organs in the body and covers substantially the entire body surface. Skin is composed of two main layers: the surface epithelium or epidermis which includes the uppermost stratum corneum, and the subjacent connective tissue layer or dermis. The skin has a number of functions such as protecting an organism from injury and dessication, receiving environmental stimuli, excreting various substances, regulating body temperature and helping to maintain water balance. Because of its quantitative and qualitative importance, substantially intact and healthy skin is crucial not only for the well being of an organism but for its very survival.

The health and integrity of skin may be compromised by wounds, abrasions, ulcers, burns, infections, irritations, premature birth and other conditions for which normal skin production and repair processes may be inadequate. For example, acute conditions such as patients who are burned over a large surface area often require immediate skin replacement. Less life-threatening but chronic skin problems such as decubitus ulcers or irritations from diaper rash may progress to more severe conditions if left untreated or if they occur in a neonate or a geriatric patient. Skin treatments encompass a variety of methods and products. These may range from symptomatic treatments such as the use of topical anti-inflammatory compounds to the use of replacement skin. For various physiological, medical, and other reasons, however, none of these treatments meet the desired goal of utilizing the body's own healing and repair system to promote its own skin growth and maturation.

Vernix caseosa (vernix) is a naturally occurring skin protectant. Vernix is a lipid rich substance composed of sebum, epidermal lipids, and desquamated epithelial cells that covers the skin of the developing fetus in utero while the fetus is completely surrounded by amniotic fluid. Vernix consists of hydrated cells dispersed in a lipid matrix. This lipid matrix undergoes a transition to a more fluid form at physiological temperatures and with the application of shear forces, such as those encountered with movement. Vernix is a covering for the skin of the fetus that resembles the stratum corneum except that it lacks multiple rigid desmosomal connections. Consequently, vernix exhibits a viscous fluid character.

The lipid component of vernix has been reported in Stewart et al., *J. Invest. Dermatol.,* 78:291–295 (1982); Nicolaides, *Lipids* 6:901–905 (1972); Haahti et al., *J. Clin. & Lab. Investigation,* 13:70–73 (1961); Karkkainen et al.,*J. Invest. Dermatol.,* 44:333–338 (1965); and U.S. Pat. No. 5,631,012, each of which are incorporated by reference herein in their entirety. Lipids, defined herein as fats or fat-like substances, include lecithin and other phospholipids, squalene, waxes, wax esters, sterol esters, diol esters, triglycerides, free sterols and four classes of fatty acids ranging in chain length from $C_{12}$ to $C_{26}$ (straight chain saturated, straight chain unsaturated, branched chain saturated, and branched chain unsaturated).

Because of its anticipated skin maturation and protectant properties, vernix appears to have promise as a clinically effective therapeutic agent. Application of vernix to clinical use, however, has been limited by its physical properties. While vernix in utero is a tractable semi-solid, vernix ex utero is a nonhomogeneous intractable compound with a consistency comparable to cheese or hardened cake frosting. Vernix is not completely soluble in conventional solvents such as absolute ethanol, 95% ethanol, 2-propanol, and combinations of chloroform and methanol. Thus, controlled and uniform administration of vernix to a surface is difficult. It has been reported that the surfactant polysorbate 80 (Tween 80) may solubilize vernix, but Tween 80 is toxic to living cells and therefore cannot be used clinically. Although there have been isolated reports of vernix directly scraped from a newborn baby for smearing over wounds (SU Patent No. 1718947A) or in an artificial lipid composition for use as a cosmetic moisturizer (U.S. Pat. No. 5,631,012), vernix in a therapeutic or prophylactic, natural or synthetic composition has not yet been reported.

While the barrier function and skin growth and maturational properties of vernix render it clinically useful to treat a variety of acute and chronic conditions, its physical properties have heretofore prevented its controlled administration in a clinical environment for therapeutic or prophylactic use. A need thus exists for a clinically useful vernix formulation.

SUMMARY OF THE INVENTION

This invention is directed to a composition comprising a normally intractable composition approximating vernix and a dispersing agent to render the vernix composition tractable. The composition may be a natural or synthetic vernix composition of about a 10% lipid fraction, about a 10% protein fraction, and about an 80% water fraction. Any or all of the water fraction may be removed and re-added to the composition. At least a portion of the lipid and protein fractions are cellular components, either of biologic or synthetic origin. The composition may have a skin curative or protectant effect and may be a film that is either free-standing or supported on a physiologically acceptable substrate. The substrate may be permeable and may include, for example, a diaper, a wound dressing, or a feminine hygiene product.

This invention is also directed to a method of enhancing growth and maturation of an epithelial layer of cells by applying a nontoxic film consisting essentially of vernix with a thickness of about 10 μm to about 500 μm to cover the epithelial cell layer and maintaining the film on the cell layer under growth enhancing conditions until a mature epithelial cell layer is obtained. The film thickness may be up to about 500 μm. The film may be applied to epithelial cells, and particularly may be applied to epidermal cells and tissues from the cornea, vagina, gastrointestinal tract, buccal cavity and other mucous membranes. The film may be applied to cells growing either in vivo or in vitro, and may be applied either directly to the cells or supported on a substrate.

This invention is further directed to a method of producing a nontoxic vernix film by dispersing vernix in a liquid such as a biocompatible liquid to form a dispersion containing vernix in a film-forming amount and applying the dispersion to a physiologically acceptable substrate. The biocompatible liquid may be, for example, dimethylsulfoxide (DMSO) or an amniotic fluid composition or a nonpulmonary surfactant composition. The amniotic fluid composition may include lecithin or other phospholipids, bile salts, mineral salts, urea, growth factors, pulmonary surfactant proteins, and combinations thereof. A preferred dispersion comprises vernix in the range of about $5\%^{w/v}$ to about $20\%^{w/v}$ in about 100% DMSO with DMSO removed after being applied to the substrate. Another preferred dispersion comprises a pulmonary surfactant composition. Still another preferred dispersion comprises a lipid composition to which pulmonary surfactant proteins have been added.

The invention is still further directed to a product contacting an epithelial layer such as skin or other tissue-contacting product comprising a nontoxic vernix composition. The skin or other tissue contacting product may be supported on a permeable substrate such as, for example, a diaper, a wound dressing, or a feminine hygiene product.

The invention is still further directed to a nontoxic fluid having a composition approximating vernix with the composition dispersed in a liquid such as a biocompatible physiologically acceptable liquid for treating a layer of epithelial cells.

The invention is additionally directed to a method of preparing a nontoxic fluid consisting essentially of vernix and dispersing a therapeutically effective amount of vernix in a liquid such as a biocompatible physiologically acceptable liquid. The biocompatable liquid may be, for example, a surfactant such as pulmonary surfactant or ionic or non-ionic surfactant, DMSO or an amniotic fluid composition. The amniotic fluid composition may include lecithin and other phospholipids, bile salts, mineral salts, urea, growth factors, pulmonary surfactant proteins, and combinations thereof. A preferred dispersion comprises vernix in the range of about $5\%^{w/v}$ to about $20\%^{w/v}$ in about 100% DMSO with DMSO removed after being applied to the substrate, or pulmonary surfactant or biocompatable ionic or nonionic surfactants.

The invention is also directed to a medical device comprising a normally intractable composition approximating vernix and a dispersing agent to render the composition tractable.

The invention is finally directed to a method of treating skin or epithelial cells or other tissues by applying a nontoxic film, consisting essentially of vernix in a film forming amount and having with a thickness of about 10 $\mu$m or up to about 10 $\mu$m to about 500 $\mu$m, to a layer of epithelial cells to provide a skin or other tissue curative and/or a skin or other tissue protectant effect, and maintaining the film on the layer of cells under growth enhancing conditions until a mature epithelial layer of skin or other tissue is obtained.

These and other methods and compositions will be apparent in light of the following detailed description and examples.

DETAILED DESCRIPTION OF THE PREFERRED EMBODIMENT

Figure 1:
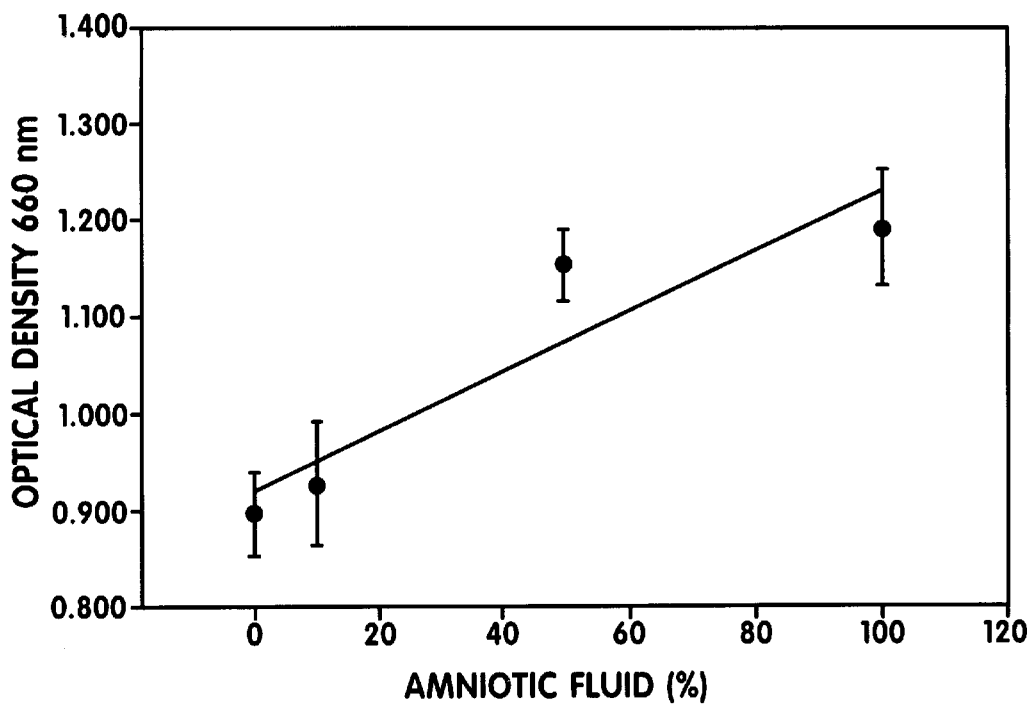
FIG. 1 is a graph showing the effect of amniotic fluid on vernix dispersion.

A nontoxic vernix film and methods of producing and using the film as a therapeutic agent are described. A therapeutic agent or drug is defined as one that is used to treat a preexisting or impending condition or to affect a structure and/or function of the body. The treatment may be prophylactic, curative, protective, maturation enhancing or combinations of these. In contrast to a therapeutic agent, a cosmetic agent is defined as one that brings about an improved appearance but with no mandatory claims to efficacy.

Vernix compositions may be natural or synthetic. Natural vernix was obtained from a newborn infant at the time of delivery. Natural vernix comprises about a 10% lipid fraction by weight, about a 10% protein fraction by weight, and about an 80% volatile fraction by weight. At least a portion of the lipid and protein fraction are cellular components, for example, corneocytes. A synthetic vernix composition may be partially synthetic or totally synthetic. Synthetic vernix comprises about a 5–15% lipid fraction by weight and about a 5–15% protein fraction by weight. In a hydrated state, there is about a 60–80% water fraction by weight. The water fraction may be removed to comprise as little as about 10% water, however, to prepare a partially or substantially dehydrated form of vernix.

As previously described, the lipid fraction of vernix has been reported to comprise lecithin and other phospholipids, squalene, waxes, wax esters, sterol esters, diol esters, triglycerides, free sterols and four classes of fatty acids ranging in chain length from $C_{12}$ to $C_{26}$ (straight chain saturated, straight chain unsaturated, branched chain saturated, and branched chain unsaturated). The lipid fraction may contain, with the relative percentages indicated, squalene (9%), aliphatic waxes (12%), sterol esters (33%), diesters (7%), triglycerides (26%), free sterols (9%), and other lipids (4%). The fatty acids within the aliphatic waxes may be branched and the branched fatty acids may be methylated. The protein fraction consists of epidermally derived proteins, primarily keratin and filaggrin. The protein fraction also contains trace amounts in the range of about micromolar to millimolar concentrations of regulatory proteins such as epidermal growth factor, and trace amounts of about nanomolar to micromolar concentrations of surfactant protein such as surfactant associated protein-A and surfactant associated protein-B. The volatile fraction is primarily water. The rate of evaporation of volatile components is relatively slow, presumably due to the low rate of water vapor transmission through the lipid matrix or increased energy requirements for the dissociation of hydrogen bonds to change water from the liquid to the gaseous state. Vernix is an odorless material, again indicating the absence of volatile carbon or nitrogen containing compounds.

In a preferred embodiment, a biologically compatible liquid may be used to disperse vernix to form a film. As used herein, a biologically compatible liquid is one that is physiologically acceptable and does not cause cellular injury. Such liquids preferably include biologically compatible surfactants including pulmonary surfactant that is either naturally occurring, synthetic or partially synthetic, and non-pulmonary surfactants including, for example, the ionic fatty acids and phospholipids and the nonionic triglycerides. Alternatively, in a less preferred embodiment, a non-biocompatable surfactant may be used in forming the film after which all traces of the non-biocompatible surfactant are removed before use of the film on or in a biological system.

A partially synthetic vernix may be produced by mixing one part of natural vernix, removed from the infant at the time of delivery, with any of the following components in the proportions indicated:either about 0.005 to about 0.05 parts phospholipid, or trace amounts of about nanomolar to micromolar concentrations of pulmonary surfactant proteins such as surfactant associated protein-A and/or surfactant associated protein-B, or 5 parts dimethylsulfoxide (DMSO), or 1 part amniotic fluid, or combinations of the above. Amniotic fluid is a composition that preferably includes water, lecithin, bile salts, mineral salts such as calcium, phosphorous and sodium salts, and pulmonary surfactant protein, and may also additionally contain growth factors and urea.

Alternatively, synthetic vernix may also be produced by combining lipids to comprise about a 10% fraction of the entire volume, proteins to comprise about a 10% fraction of the entire volume, and water to comprise the remaining about 80% of the entire volume. The lipid fraction is about 10% but may be in the range of about 5–15% of the total composition. The following lipid components are combined in the relative percentages indicated: squalene (9%), aliphatic waxes (12%), sterol esters (33%), diesters (7%), triglycerides (26%), free sterols (9%), and other lipids (4%). The fatty acids within the waxes may be branched and the branched fatty acids may be methylated. The protein components, combined to constitute about a 10% fraction but in the range of about 5–15% of the total composition are epidermally derived proteins, primarily keratin and filaggrin, with trace amounts of about micromolar to millimolar concentrations of regulatory proteins such as epidermal growth factor, and trace amounts of about nanomolar to micromolar concentrations of surfactant protein such as surfactant associated protein-B and surfactant associated protein-B.

The cellular component of vernix may be of biologic or synthetic origin and may serve several functions. One function may be as an aid in the moisture delivery and/or moisture retention aspects of the disclosed composition. Cells, for example skin epithelial cells in general and corneocytes in particular, may serve as vehicles for the slow release of water which supplies moisture to an appropriate tissue such as skin.

Another function may be incorporation of cellular components that have been modified, selected or bioengineered to perform a particular function. For example, keratinocytes that have been genetically modified are grown in culture and in the process of maturation, the genetically modified keratinocytes are terminally differentiated and are incorporated into vernix. Vernix, containing the genetically modified mature keratinocytes, is then used as a therapeutic agent to treat diseases of the skin where the gene products are needed. For example, as reported in J. Invest. Derm., 103, p. 76S–84S, 1994, it is known that genes for the following proteins have been successfully transduced into cells of the skin:growth hormone, insulin, transferrin, human β-chorionic gonadotropin, chloramphenicol acetyl transferase (CAT), factor VIII, factor IX, and adenosine deaminase. Systems shuttling such genetically modified fibroblasts and/or keratinocytes are available and have undergone clinical testing. Symptoms of monopolysaccharide (MPS) storage disorder have been corrected in mice by transducing the human β-glucuronidase gene into MPS VII fibroblasts that were placed into a shuttle of collagen coated Teflon and transplanted intraperitoneally.

As another example, differentiated keratinocytes may be bioengineered to restore or provide enhanced barrier function. A vernix composition containing these cells may be applied at the site of a burn or deep wound where immune function has been destroyed. A vernix composition containing bioengineered cells may be applied to the exposed skin surface of occupationally-exposed workers. The vernix would act as a surface barrier to prevent penetration of the toxins into the skin and may also degrade or render the toxins less harmful. The composition could then be removed from the exposed skin upon completion of the exposure, for example, by washing the hands and forearms whereby the vernix composition containing the toxins would be removed. The composition could be used either alone or as an additional barrier with gloves.

As yet another example, some or all of the cellular elements of vernix may be provided to the composition upon application to a physiologic surface. In this way the composition may be partially or completely "customized" for a particular individual or type of individual. The components of vernix may be provided in cells of biologic or synthetic origin such as in vehicle delivery systems, which may be termed manufactured or synthetic cells. Such manufactured delivery systems could be, for examples, capsules such as agarose capsules, liposomes, vesicles, etc.

For some applications a vernix composition may contain an antimicrobial or an antiinfective that would bind to microorganisms and facilitate their clearance from the site of application of the composition. The application site may be a compromised surface such as a wound in which case the vernix-antimicrobial composition would be used as a therapeutic curative agent, or the application site may be an intact surface such as skin in which case the vernix-antimicrobial composition would be used as a therapeutic barrier prophylactic agent. A preferred anti-infective for incorporation into a vernix composition is surfactant associated protein-A, which is prevalent in lung and amniotic fluid.

Either natural or synthetic vernix must be rendered tractable and dispersible. A vernix dispersion, wherein vernix may not be in a true solution but may be in a number of different states, includes a suspension, a solid, or a semi-solid. In one embodiment which is preferred, pulmonary surfactant protein is combined with vernix. In another embodiment, natural vernix in amounts sufficient to yield concentrations of $5\%^{w/v}$, $10\%^{w/v}$ or $20\%^{w/v}$, was added to either 50% or 100% dimethylsulfoxide (DMSO). The DMSO solvent was selected since it is an organic solvent that is routinely used in the preinoculation processing of cultured skin substitutes. Additionally DMSO is a well-known penetrant for the delivery of exogenous substances through the skin, indicating that DMSO is miscible with skin lipids and presumably is miscible with vernix. Finally, DMSO is a relatively volatile compound that is easily removed by evaporation. Mixtures of vernix and DMSO were sonicated at room temperature under a fume hood until the vernix was completely dispersed using a Cole-Parmer sonicator (Chicago, Ill.).

The extent of vernix dispersion was evaluated by monitoring its absorbance at 600 nm using a standard spectrophotometer. An increase in light absorbance indicated a more complete dispersion of vernix in the solvent. Conversely, an increase in light transmittance (decreased absorbance) indicated clumps of vernix in the solvent.

A mixture of $5\%^{w/v}$ vernix in 50% DMSO was evaluated. Visible clumps persisted even after the mixture was sonicated for several minutes. A mixture of $5\%^{w/v}$ vernix in 100% DMSO was evaluated. Increasing the DMSO concentration resulted in less clumping although a slurry, rather than a solution, was obtained. When the vernix concentration was increased to either $10\%^{w/v}$ or $20\%^{w/v}$ vernix in 100% DMSO, the resulting dispersion was viscous but appeared void of clumps. Thus, $20\%^{w/v}$ vernix was deemed the preferred concentration for ease in handling. Agitation of the $20\%^{w/v}$ vernix in 100% DMSO resulted in a relatively uniform mixture.

The dispersion of $20\%^{w/v}$ vernix in 100% DMSO prepared as described above was formed into a film and applied to a biocompatible substrate as will be described below. The DMSO was evaporated by exposing the dispersion to a vacuum at room temperature (approximately 22° C.) for a period of time between 72 and 168 hours. In one embodiment, the solvent used was amniotic fluid, obtained from a newborn at the time of delivery. Amniotic fluid is known to contain factors such as pulmonary surfactant and phospholipid such as lecithin that may aid in vernix dispersion. In another embodiment, the solvent was the commercially available pulmonary surfactant Survanta® (Abbott Laboratories, Inc., Columbus, Ohio). Combinations of these or their individual constituents or other physiologically acceptable solvents may also be used.

In one embodiment, vernix dispersed in a biocompatible liquid was applied to a physiologically acceptable support structure in a liquid state to form a vernix film. A film is defined herein as an interfacial surface covering, in either a liquid or a solid state, with temperature-dependant properties. Film-forming techniques include but are not limited to spraying, extruding, blowing, pouring, evaporating, coating and painting. The vernix dispersion may be presented as droplets which coalesce to form a film upon encountering the support.

In an alternate embodiment, a preformed vernix film is applied to a support. The physiologically acceptable support structure is one that can withstand sterilization, preferably by standard sterilization techniques known to one skilled in the art such as exposure to gamma radiation, autoclaving, and so on. The support structure is not limited to a particular composition or configuration and, depending upon its use, may or may not be sterilized and may take various forms. In one embodiment, the nontoxic vernix film is used to enhance skin cell maturation and may be applied to structures such as filters, membranes, beads, particles, and so on. Similarly, the support structure is not limited to a particular state of matter and may be a solid, a semi-solid, a gel and so on. In one embodiment, the support consists of a nylon monofilament interpositional surfacing material such as Interfaces pads (Winfield Laboratories, Inc., Dallas Tex.), Biobrane II® (Sterling Drug Inc., New York, N.Y.) or circular nylon filters of suitable porosity (Micron Separations Inc., Westboro, Mass.). Other support materials, however, could also be used to practice the invention such as glass fiber filters and collagen-glycosaminoglycan support matrices.

In another embodiment, the nontoxic vernix film is used to promote wound healing and/or tissue repair and may be applied to various materials for placement either in direct contact or indirect contact with a skin site requiring treatment such as a wound, an abrasion, an ulcer such as a gastrointestinal ulcer or a skin ulcer, a burned area, a site of infection or irritation, a wart and so on. The support structure may be permeable to physical and/or chemical agents, and may take a variety of forms, depending upon its purpose and the extent of the area requiring dressing or treatment. The nontoxic vernix film may be applied to various synthetics such as thermoplastic films, blown films and breathable films, and various natural and synthetic fabric compositions such as woven, non-woven, spun, and stitched fabrics. The invention may be used in a variety of products, examples of which include wound dressings and coverings such as bandages, tapes, gauze, adhesive products applied for a short or long term to the skin, ostomy care products, hospital pads such as incontinent pads, absorbent pads, and examination pads, disposable and cloth diapers, and feminine hygiene products such as intralabial devices.

The vernix composition of the invention may be used therapeutically to promote skin growth, skin maturation, skin barrier formation, wound healing, skin flexibility, and tissue repair. The vernix composition of the invention may also be used as a skin protectant to augment and/or promote skin barrier function, skin barrier formation, skin moisture retention, skin moisture delivery and skin flexibility.

The invention will be further appreciated in light of the following examples.

EXAMPLE 1

A dispersion of $20\%^{w/v}$ vernix in 100% DMSO was prepared with sonication and agitation to form a homogenous mixture. Nine 2-mm holes were drilled into the bottom of each well of a standard six-well polystyrene tissue culture plate (Becton Dickinson Labware, Bedford, Mass.). A singular circular sterile nylon filter, 20 micron porosity, 25-mm diameter (Micron Separations Inc., Westboro, Mass.) was placed into each well. The nylon filters were coated with vernix by first pipetting one ml of the $20\%^{w/v}$ vernix solution onto the top of each filter. Excess liquid was then wicked out of the wells through the filters on the bottom of the plate using paper towels. Finally the remainder of the liquid was evaporated by placing the culture plate in a vacuum chamber for a period of between 72 and 168 hours. The vernix-coated filters were then sterilized by gamma-irradiation at 17 kGy for use in skin culture Cultures of human skin were prepared by a standard technique inoculating human keratinocytes onto a fibroblast-impregnated collagen-glycosaminoglycan support. Cultures were assessed weekly for epidermal barrier formation by surface electrical capacitance using a dermal phase meter (Nova Technology Corporation, Gloucester, Mass.) and were sampled weekly for histology and mitochondrial enzyme activity. In addition, the conditioned culture medium was sampled daily for glucose and lactate levels. In one embodiment, three-day old cultured human skin substitutes were overlaid with the vernix coated nylon filter.

EXAMPLE 2

With reference to FIG. 1 the effect of amniotic fluid on the dispersion of native vernix is shown. Amniotic fluid from a term delivery was diluted with Hank's Balanced Salt Solution (HBSS, Life Technologies, Gaithersburg, Md.) to a final concentration of either $10\%^{w/v}$ or $50\%^{w/v}$l Undiluted HBSS and amniotic fluid were also evaluated. One hundred mg vernix was added to ten ml of each of the 10% or 50% solutions, undiluted HBSS and undiluted amniotic fluid contained in four 16×100 mm plastic culture tubes. The mixtures were incubated at 37° C. for 1 hour, sonicated (Model 300, Fisher Scientific, Pittsburgh, Pa.) at room temperature for three minutes then mixed by vortexing. The optical density at 660 nm ($OD_{660}$) was measured and plotted against the concentration of amniotic fluid in the solution.

As shown in FIG. 1, there was a direct correlation between the concentration of amniotic fluid in a solution and its turbidity ($r^2$=0.6773). Turbidity of control solutions were subtracted to account for background turbidity. With 0% amniotic fluid (HBSS alone) the $OD_{660}$ was 0.900. At concentrations of 10%, 50% and 100% amniotic fluid, the $OD_{660}$ increased linearly. The increase in turbidity at increased concentrations of amniotic fluid reflected better dispersion of native vernix in the presence of amniotic fluid.

EXAMPLE 3

The effect of pulmonary surfactant on dispersion of native vernix was analyzed. It is well known that a correlation exists between increased turbidity of amniotic fluid with increased gestational age of a fetus. Therefore, it was hypothesized that increasing the concentration of a surfactant of pulmonary origin would induce a "roll-up" phenomenon of vernix with secondary detachment of vernix and a resultant increase in turbidity. The roll-up phenomenon is a term used to describe the interdigitation of surfactant molecules between a substance of primarily lipid composition and the surface to which it has adhered. As surfactant molecules migrate progressively into the space, they displace the lipid substance from the surface causing it to roll up and move in to the surrounding liquid.

One hundred mg of native vernix was applied to the interior wall of a 1.5 ml plastic microcentrifuge tube using a positive displacement pipet and was spread with a glass pestle to form a uniform coating. One ml of normal saline containing either 50, 100 or 200 µg of a phospholipid (lecithin derived from Survanta®, was added to each tube. Survanta® is a clinically used pulmonary surfactant suspension. Tubes were gently agitated by turning slowly (Labquake® rotisserie, Labindustries, Inc. Berkeley, Calif.) at 37° C. overnight. The liquid was then decanted and was analyzed in a spectrophotometer at 600 nm to determine solution turbidity, with increased turbidity reflecting increased release of vernix from the wall of the microfuge tube.

Figure 2:
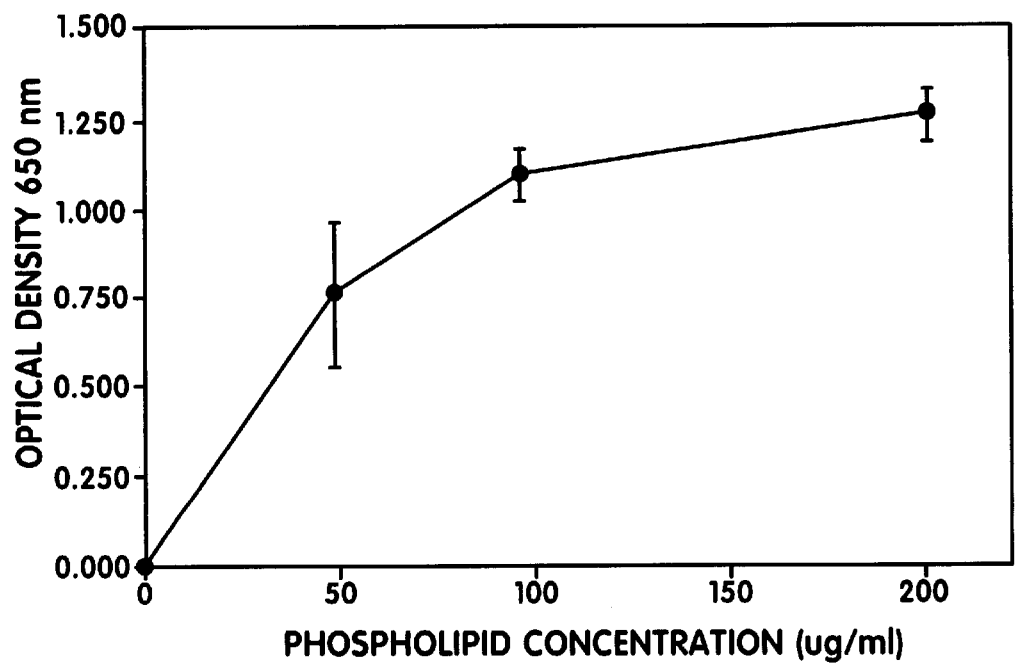
FIG. 2 is a graph showing the effect of pulmonary surfactant on vernix dispersion.

As shown in FIG. 2, an increase in solution turbidity was obtained at increasing phospholipid concentrations. The bars at each concentration reflect the mean $OD_{660}$ plus or minus the standard error of the mean (SEM).

EXAMPLE 4

Rehydration experiments were performed to determine hygroscopicity of vernix following drying. Vernix samples were thinly coated onto Cahn electrobalance aluminum pans (13 mm diameter, Cahn Instruments, Inc., Cerritos, Calif.) for drying. The samples were desiccated under vacuum at 23° C. for 1 week to a constant weight. The desiccated samples were submersed in either deionized water or normal saline contained in tissue culture plate wells. Rehydration was performed in a humidified environment thermoregulated to 37° C. for either 24 hours or ten days.

Figure 3:
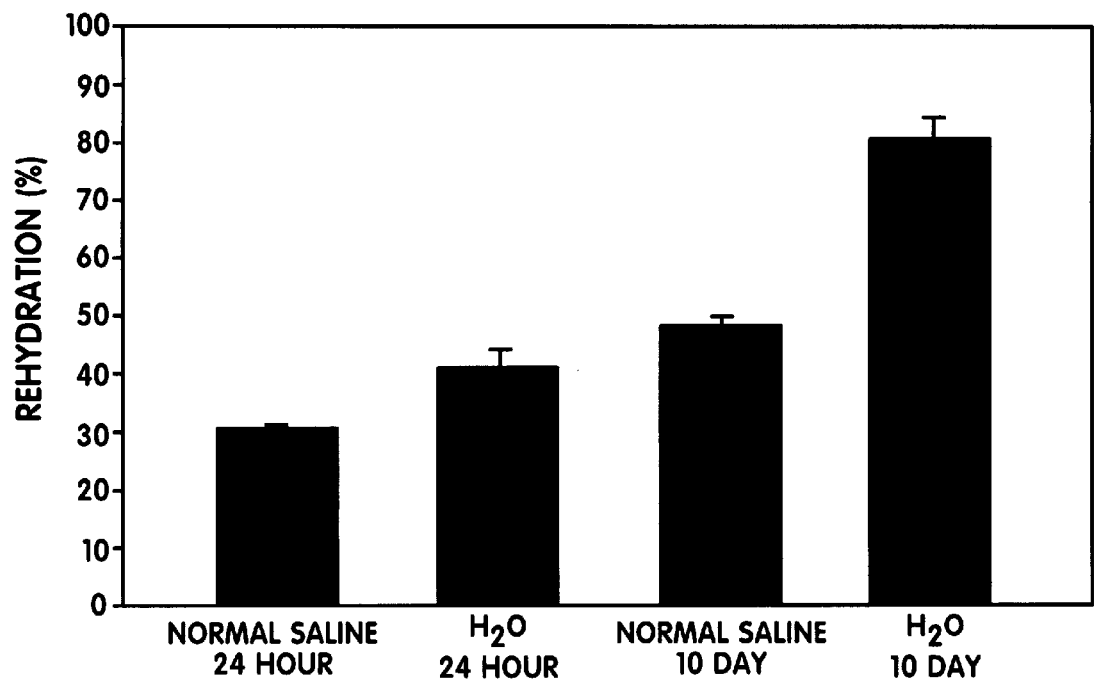
FIG. 3 is a graph showing vernix rehydration.

The results are shown in FIG. 3, with the bars above each time point representing the SEM. At either 24 hours or ten days, deionized water was a better hydration medium than normal saline. At 24 hours deionized water resulted in 39.4% +/−2.9% rehydration, while normal saline resulted in 28.1% +/−0.4% rehydration. At ten days deionized water resulted in 79.3% +/−4.1% rehydration, while normal saline resulted in 46.4% +/−2.1% rehydration. These data are consistent with normal saline having a relatively higher osmotic composition compared to deionized water, and the hypothesis that it is the cellular elements that are the hydrating elements. The rehydration rate in either normal saline or deionized water was consistent with the slow release and slow reaccumulation of water in desiccated vernix.

EXAMPLE 5

Figure 4:
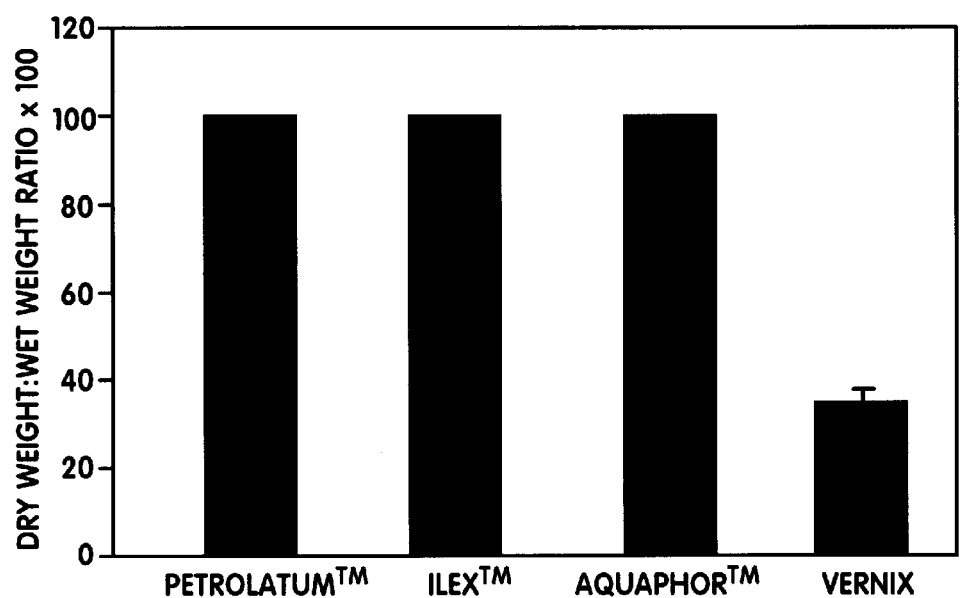
FIG. 4 is a graph comparing the water content of vernix with commercial barrier creams.

With reference to FIG. 4 the water content of vernix was compared with the water content of commercial barrier creams such as Petrolatum® (CVS, Woonsocket, R.I.), Ilex® (E. R. Squibb & Sons, Inc., Princeton, N.J.) and Aquaphor® (Beiersdorf, Norwalk, Conn.). The vernix analyzed had been stored for several days to several weeks. A ratio of the dry weight to the wet weight was obtained for each substance.

As shown in FIG. 4, the dry weight:wet weight ratios for Petrolatum®, Ilex® and Aquaphor® were each 100%. The dry weight:wet weight ratio of vernix was about 40%, indicating that about 60% of the material in vernix was volatile. When vernix was analyzed shortly after birth of term infants, the dry weight:wet weight ratio indicated that approximately 80% of vernix was volatile. This volatile fraction was not observed in the other barrier creams. The volatile fraction was initially broadly interpreted as moisture content, which comprises substances that can vaporize and lead to weight loss of the sample.

To determine whether the volatile fraction was specifically water, a Karl-Fisher volumetric titration was performed using a titrator (Model DL-18, Mettler-Toledo International, Inc., Greifensee, Switzerland). This technique is highly selective for water determination and is based on the chemical reaction of water with iodine added volumetrically as titrant. The method allows determination of water as low as 1 part per million (ppm) up to 100%. Analyses were performed in triplicate on fresh vernix samples collected from three term infants. The results indicated that the maximum water content of freshly harvested vernix was $82.0\%^{w/v}$+/−$0.5\%^{w/v}$.

EXAMPLE 6

Figure 5:
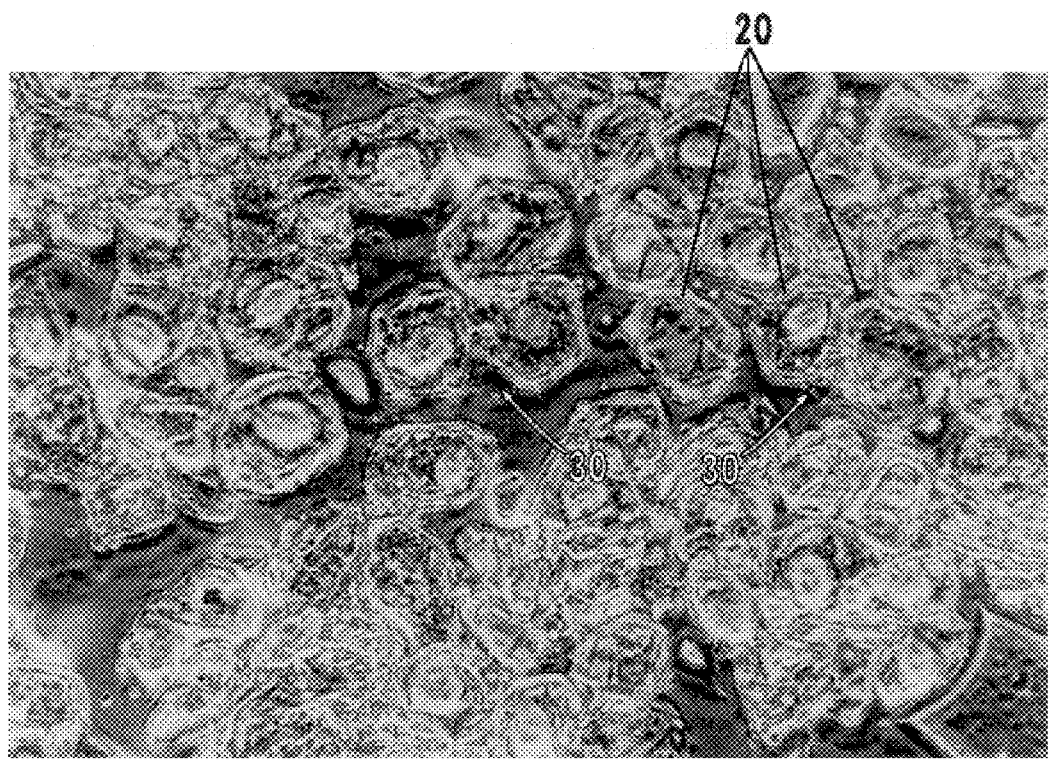
FIG. 5 is a phase contrast image of fresh vernix.

Fresh vernix was analyzed by phase contrast microscopy at 500× magnification. As shown in FIG. 5, there is dense packing of fetal corneocytes 20 surrounded by a presumptive lipid matrix 30.

EXAMPLE 7

Human vernix was fixed in glutaraldehyde (2%) and paraformaldehyde (2%) in 0.1 M sodium cacodylate buffer (pH 7.4). The fixed specimen was subsequently treated with osmium tetroxide (1%) in 0.1M sodium cacodylate buffer and was then embedded in epon (12.3 g glycerol polyglycidyl ether, 3.3 g dodecenyl succinic anhydride, 8.7 g nadic methyl anhydride, 0.40 g 2-,4-,6-tri(dimethyl-aminomethyl) phenol, Ted Pella Inc., Redding, Calif.). Specimens were sectioned and examined by transmission electron microscopy.

Figure 6:
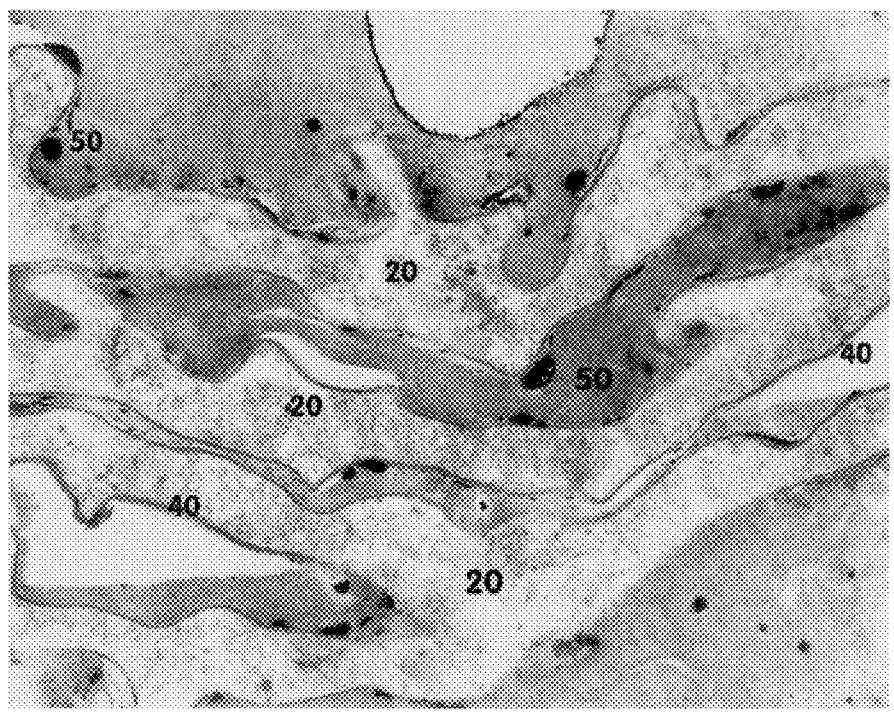
FIG. 6 is a photomicrograph of human vernix analyzed by transmission electron microscopy.

As shown in FIG. 6, a large number of fetal corneocytes 20 were observed throughout the specimen. These corneocytes 20 showed little evidence of tonofilament orientation and the tonofilament density was less than that observed in adult corneocytes. There were no apparent desmosomes and no obvious nuclei. The corneocytes 20 were surrounded by an electron-dense "membrane" or cornified cell envelope 40. When compared to adult stratum corneum, there appeared to be increased corneocyte malleability as evidenced by the curvature of the corneocytes 20. Also noted were unidentified black bodies 50 in the putative lipid areas 30 which may be sebocyte debris.

EXAMPLE 8

Figure 7:
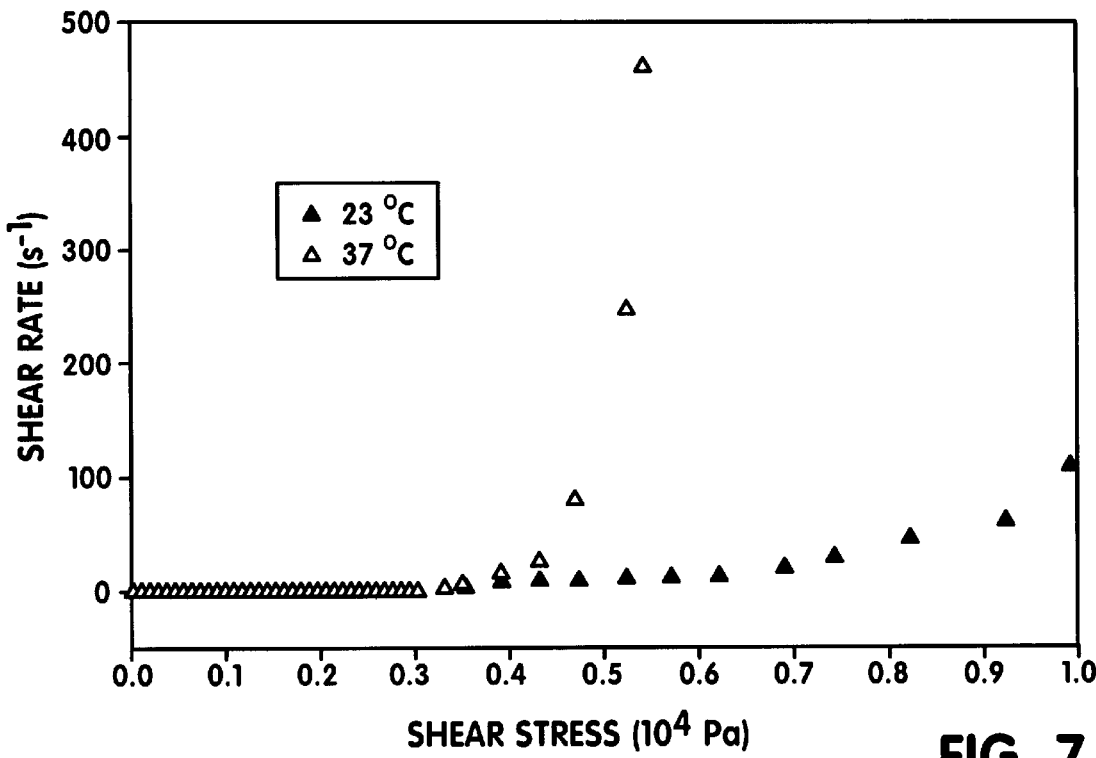
FIG. 7 is a graph showing the effect of temperature on rheological properties of vernix.

With reference to FIG. 7 the effect of temperature on rheological properties of vernix was determined. Shear stress was plotted against shear rate. Rheological measurements of human vernix were performed on a controlled stress rheometer with a circulating water bath temperature control (Model RS150, Haake & Partner Datentechnik GMBH, Offenburg, Germany). The rheometer was connected to a controlled temperature water bath for determination of shear stress versus shear rate over a range of physiological temperatures (23° C. to 37° C.). The sensor system was a 20 mm diameter parallel plate with measurement gap set to 1.00 mm. The measurement program consisted of a stress ramp from 1.0 to 10,000 pascals (Pa) over three minutes, following a five minute equilibration period. Measurements were nondestructive and required about 0.5 g of vernix.

FIG. 7 illustrates the effect of ambient temperature on the stress flow curves for human vernix. At body temperature (37° C., open triangles) vernix behaves as a relatively fluid material with a yield value occurring at about 4000 Pa. When the same sample was analyzed at room temperature (23° C., closed triangles) vernix exhibited a minimum tendency to deform and flow even at the highest tested level of 10,000 Pa. Thus, vernix has improved deformation and flow characteristics at 37° C. versus at 23° C.

EXAMPLE 9

The rheological behavior of a mixture of vernix and pulmonary surfactant was evaluated using the same system as in Example 8. About 500 mg of vernix was mixed with 0.5 ml Survanta®, a mixture of lecithin and other phospholipids containing pulmonary surfactant proteins and standardized to a concentration of 25 mg phospholipid per ml. Rheological measurements were performed as in Example 8.

Figure 8:
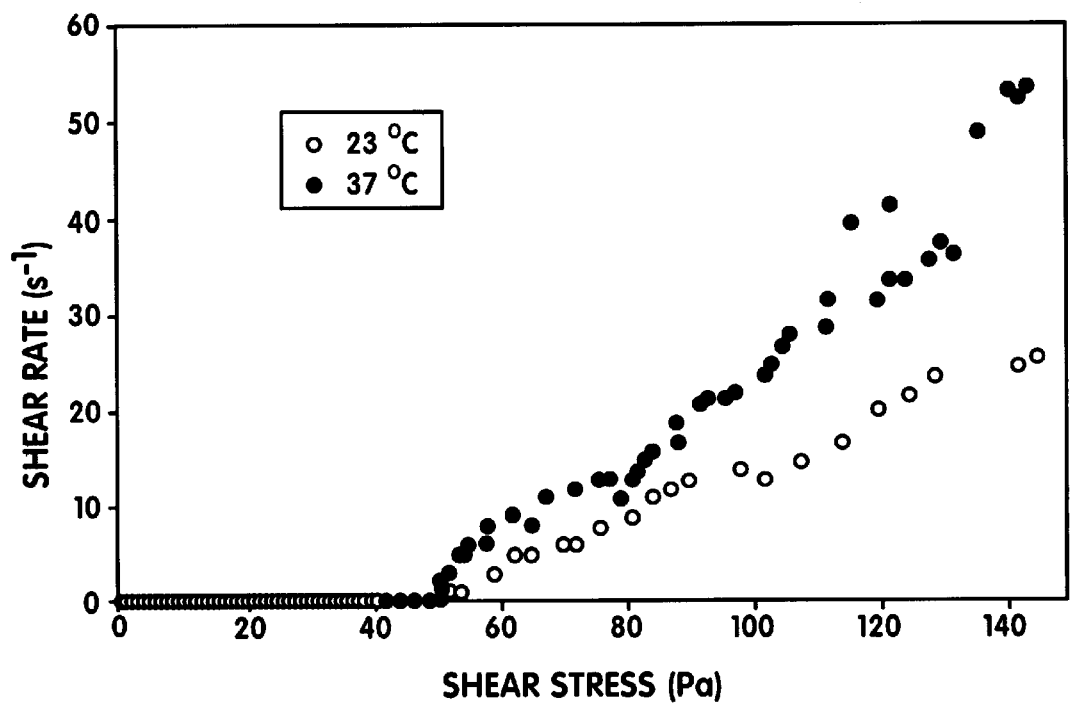
FIG. 8 is a graph showing rheological properties of a vernix-pulmonary surfactant mixture.

As shown in FIG. 8, the addition of Survanta® markedly modified the resulting vernix stress flow curves obtained at both room temperature (23° C., open circles) and body temperature (37° C., closed circles). In a vernix-pulmonary surfactant mixture, as opposed to vernix alone, much lower applied stress (about 50 Pa) was required to induce flow in vernix. This result is likely to be physiologically significant since pulmonary derived phospholipids and proteins are known to increase in amniotic fluid in the later part of gestation.

EXAMPLE 10

Figure 9:
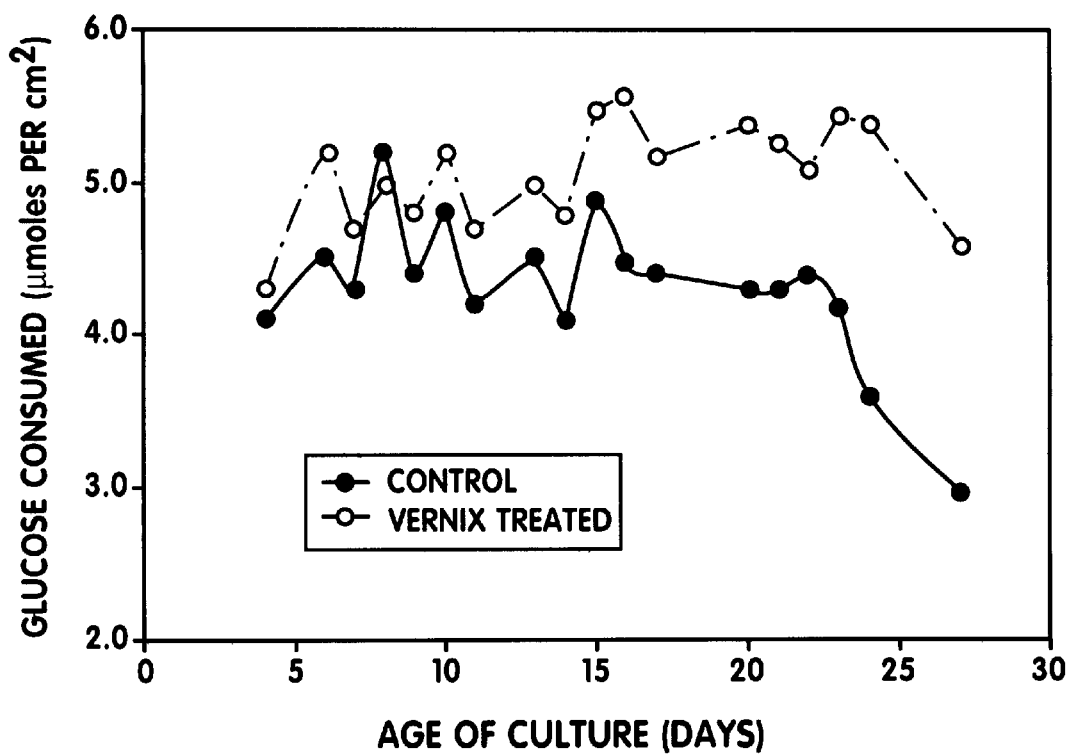
FIG. 9 is a graph of glucose consumption by cultured skin substitutes with and without a vermix covering.

With reference to FIG. 9, glucose consumption by cultured skin substitutes (CSS) was determined. CSS were prepared by sequential inoculation of human fibroblasts and keratinocytes onto collagen-glycosaminoglycan substrates. Cultures were incubated with (open circles) and without (control, closed circles) an overlying covering of human vernix applied to a thin microporous nylon membrane that was placed on the top of the CSS on the third day of incubation. Conditioned culture media were collected daily at the time of media change and glucose measurements were performed on a glucose lactate analyzer (Stat 2300, YSI, Yellow Springs, Ohio). Glucose consumption was consistently higher in the vernix-treated cultures, indicating increased cellular metabolism in the vernix-treated CSS. This suggested a growth-promoting effect of the vernix application.

A nontoxic vernix film and methods of producing and using the film are thus disclosed. In addition, a vernix dispersion and methods of producing and using the dispersion are disclosed. The compositions and methods of the invention may be used for skin cell maturation and for wound healing and/or repair. Other variations or embodiments of the invention will also be apparent to one of ordinary skill in the art from the above description and example. For example, vernix may be formulated into a cream, such as a first aid cream, a cream for treating poison ivy or other forms of contact dermatitis, or a diaper rash cream. Thus, the forgoing embodiments are not to be construed as limiting the scope of this invention.

What is claimed is:

1. A composition comprising an intractable vernix composition and a dispersing agent to render the vernix composition tractable wherein the intractable vernix composition comprises about a 10% lipid fraction, about a 10% protein fraction, and about an 80% water fraction wherein at least part of the composition comprises cells.

2. The composition of claim 1 wherein the cells comprise corneocytes.

3. The composition of claim 1 wherein the cells are bioengineered.

4. The composition of claim 3 wherein the bioengineered cells perform a function selected from the group consisting of restoring a barrier function, enhancing a barrier function, providing a gene, providing a gene product and combinations thereof.

5. The composition of claim 1 providing a moisture delivery skin protectant effect.

6. A composition comprising a synthetic vernix composition comprising a lipid fraction in the range of about 5–15% by weight and a protein fraction in the range of about 5–15% by weight.

7. The composition of claim 6 further comprising a water fraction in the range of about 60%–80% by weight.

8. The composition of claim 6 wherein the protein fraction is provided at least in part by cells, the cells selected from the group consisting of biologic cells, synthetic cells and combinations thereof.

9. A method of enhancing growth and maturation of an epithelial layer comprising applying a nontoxic film consisting essentially of vernix and having a thickness of up to about 500 µm to cover the epithelial layer and maintaining the film on the layer under growth enhancing conditions until a mature epithelial layer is obtained.

10. The method of claim 9 wherein the epithelial layer is from a tissue selected from the group consisting of epidermis, cornea, buccal cavity, gastrointestinal tract, vagina and combinations thereof.

11. A method of producing a nontoxic vernix film comprising dispersing vernix in an amniotic fluid composition comprising components selected from the group consisting of lecithin, bile salts, pulmonary surfactant protein, urea, growth factors, mineral salts and combinations thereof.

12. A product contacting an epithelial layer, the product comprising a vernix composition containing a cellular component and a substrate.

13. The product of claim 12 wherein the cellular component is at least in part from an epithelial layer selected from the group consisting of epidermis, cornea, buccal cavity, gastrointestinal tract, vagina and combinations thereof.

14. The product of claim 12 wherein the substrate is selected from the group consisting of a membrane, a film, a fabric, a wound dressing, an adhesive product, an ostomy care product, a hospital pad, an incontinent pad, an absorbent pad, an examination pad, a diaper, and a feminine hygiene product.

15. The product of claim 12 wherein the substrate is permeable.

16. The product of claim 12 wherein the vernix composition is selected from the group consisting of a natural vernix composition or a synthetic vernix composition.

17. The product of claim 12 wherein the vernix composition is substantially nontoxic.

18. A nontoxic fluid comprising a vernix composition, the composition dispersed in a liquid for treatment of an epithelial layer and comprising a lipid fraction in the range of about 5–15% by weight, a protein fraction in the range of about 5–15% by weight, and a water fraction in the range of about 60–80% by weight wherein at least part of the composition comprises cells.

19. The fluid of claim 18 wherein the water fraction is controllably removed from the composition and subsequently restored to the composition.

20. The fluid of claim 18 wherein the cells comprise corneocytes.

21. The fluid of claim 18 wherein the cells are bioengineered.

22. The fluid of claim 21 wherein the bioengineered cells perform a function selected from the group consisting of restoring a barrier function, enhancing a barrier function, providing a gene, providing a gene product and combinations thereof.

23. The fluid of claim 18 having a skin protectant effect selected from the group consisting of a barrier function, a moisture retention function, a moisture delivery function and combinations thereof.

24. The fluid of claim 18 wherein the liquid is biocompatible.

25. The fluid of claim 24 wherein the liquid is a surfactant.

26. A medical device comprising a vernix composition, the composition dispersed in a liquid for treatment of an epithelial layer and comprising a lipid fraction in the range of about 5–15% by weight, a protein fraction in the range of about 5–15% by weight, and a water fraction in the range of about 60–80% by weight wherein at least part of the composition comprises cells.

27. The device of claim 26 wherein the cellular components comprise corneocytes.

28. The device of claim 26 wherein the cells are bioengineered to perform a function selected from the group consisting of restoring a barrier function, enhancing a barrier function, providing a gene, providing a gene product and combinations thereof.

29. The device of claim 26 wherein the vernix composition is substantially nontoxic.

30. The device of claim 26 wherein the liquid is biocompatible.

31. The device of claim 26 wherein the liquid is non-biocompatible.

32. A method of treating a tissue having an epithelial layer comprising applying a nontoxic film having a thickness of up to about 500 μm and consisting essentially of vernix in a film-forming amount to the epithelial layer to provide a treating effect, the effect selected from the group consisting of a curative effect, a protectant effect and combinations thereof; and maintaining the film on the layer under growth enhancing conditions until a mature epithelial layer is obtained.

33. The method of claim 32 wherein the epithelial layer is selected from the group consisting of epidermis, cornea, buccal cavity, gastrointestinal tract, vagina and combinations thereof.

34. The method of claim 32 wherein the film is applied to a physiologically acceptable support and the support is applied to the layer to be treated.

35. The method of claim 34 wherein the support is permeable.

36. The method of claim 34 wherein the support is selected from the group consisting of a membrane, a film, a fabric, a wound dressing, an adhesive product, an ostomy care product, a hospital pad, an incontinent pad, an absorbent pad, an examination pad, a diaper, and a feminine hygiene product.

* * * * *

UNITED STATES PATENT AND TRADEMARK OFFICE
CERTIFICATE OF CORRECTION

PATENT NO. : 6,113,932
DATED : September 5, 2000
INVENTOR(S) : Steven B. Hoath et al.

Page 1 of 1

It is certified that error appears in the above-identified patent and that said Letters Patent is hereby corrected as shown below:

Column 4,
Line 11, "vermix" should be -- vernix --

Column 8,
Line 64, "$10\%^{w/v}$ or $50\%^{w/v}$" should be -- $10\%^{v/v}$ or $50\%^{v/v}$ --

Column 10,
Line 44, "$82.0\%^{w/v}+/-0.5\%^{w/v}$" should be -- $82.0\%^{w/w}+/-0.5\%^{w/w}$ --

Signed and Sealed this

Twenty-sixth Day of February, 2002

Attest:

*Attesting Officer*

JAMES E. ROGAN
*Director of the United States Patent and Trademark Office*